(12) United States Patent
Smith

(10) Patent No.: US 9,820,861 B2
(45) Date of Patent: Nov. 21, 2017

(54) RAIL-FIXING IMPLANT

(71) Applicant: Richard Charles Smith, Rancho Palos Verdes, CA (US)

(72) Inventor: Richard Charles Smith, Rancho Palos Verdes, CA (US)

( * ) Notice: Subject to any disclaimer, the term of this patent is extended or adjusted under 35 U.S.C. 154(b) by 0 days.

(21) Appl. No.: 15/330,848

(22) Filed: Nov. 7, 2016

(65) Prior Publication Data

US 2017/0095341 A1  Apr. 6, 2017

(51) Int. Cl.
*A61F 2/46* (2006.01)
*A61F 2/42* (2006.01)
*A61F 2/44* (2006.01)
*A61B 17/17* (2006.01)
*A61F 2/30* (2006.01)
*A61F 2/38* (2006.01)
*A61F 2/40* (2006.01)

(52) U.S. Cl.
CPC ........ *A61F 2/4202* (2013.01); *A61B 17/1735* (2013.01); *A61F 2/4425* (2013.01); *A61F 2/4606* (2013.01); *A61F 2/4684* (2013.01); *A61F 2/3877* (2013.01); *A61F 2/4081* (2013.01); *A61F 2/4241* (2013.01); *A61F 2/4657* (2013.01); *A61F 2002/30115* (2013.01); *A61F 2002/30138* (2013.01); *A61F 2002/30159* (2013.01); *A61F 2002/30398* (2013.01); *A61F 2002/30616* (2013.01); *A61F 2002/30622* (2013.01); *A61F 2002/30649* (2013.01); *A61F 2002/30879* (2013.01); *A61F 2002/30883* (2013.01); *A61F 2002/4205* (2013.01); *A61F 2002/4207* (2013.01); *A61F 2002/4623* (2013.01); *A61F 2250/0059* (2013.01); *A61F 2250/0064* (2013.01); *A61F 2310/00197* (2013.01)

(58) Field of Classification Search
CPC ............ A61F 2002/30387–2002/30388; A61F 2002/30883; A61F 2002/30164; A61F 2002/30383–2002/30403; A61F 2002/30428–2002/30431; A61F 2002/30878–2002/30904; A61F 2/4202–2002/4687; A61B 17/15–17/1796

See application file for complete search history.

(56) References Cited

U.S. PATENT DOCUMENTS 3,840,904 A  10/1974  Tronzo
3,889,300 A   6/1975  Smith
(Continued)

FOREIGN PATENT DOCUMENTS

EP  1 707 157 A1  10/2006
WO  2004/0830 A2   9/2004

OTHER PUBLICATIONS

Smith et al., U.S. Appl. No. 60/998,198, filed Oct. 9, 2007 A.D.
(Continued)

*Primary Examiner* — Yashita Sharma
*Assistant Examiner* — Rebecca Preston
(74) *Attorney, Agent, or Firm* — Christopher John Rudy

(57) ABSTRACT

Implant includes a body and a utile feature, for example, a smooth articulating surface. A transverse rail stem system with a plurality of rails is provided, spaced apart from the utile feature, which is adapted for transverse insertion into a bodily substrate, for example, resected bone. A surgical template—for example, to assist in sawing, drilling with a drill bit and drill guide, and broaching with a broach—along with such bone removal tools can help prepare the bone for receipt of the implant.

13 Claims, 9 Drawing Sheets

(56) References Cited

U.S. PATENT DOCUMENTS

| | | | |
|---|---|---|---|
| 3,965,489 | A | 6/1976 | Freeman et al. |
| 4,550,450 | A | 11/1985 | Kinnett |
| 4,743,261 | A | 5/1988 | Epinette |
| 4,743,262 | A | 5/1988 | Tronzo |
| 4,936,863 | A | 6/1990 | Hofmann |
| 4,957,510 | A | 9/1990 | Cremascoli |
| 5,007,932 | A | 4/1991 | Bekki et al. |
| 5,037,440 | A | 8/1991 | Koenig |
| 5,047,059 | A | 9/1991 | Saffar |
| 5,314,486 | A | 5/1994 | Zang et al. |
| 5,702,469 | A | 12/1997 | Whipple et al. |
| 5,910,171 | A | 6/1999 | Kummer et al. |
| 6,102,953 | A | 8/2000 | Huebner |
| 6,299,647 | B1 | 10/2001 | Townley |
| 6,454,809 | B1 | 9/2002 | Tornier |
| 7,476,255 | B2 | 1/2009 | Lester et al. |
| 9,486,321 | B1 | 11/2016 | Smith et al. |
| 2002/0055784 | A1 | 5/2002 | Burstein et al. |
| 2003/0208273 | A1 | 11/2003 | Eisermann et al. |
| 2003/0233147 | A1 | 12/2003 | Nicholson et al. |
| 2004/0167631 | A1 | 8/2004 | Luchesi et al. |
| 2004/0193268 | A1 | 9/2004 | Hazebrouck |
| 2005/0143834 | A1 | 6/2005 | Lester et al. |
| 2006/0025866 | A1 | 2/2006 | Scrafin, Jr. et al. |
| 2006/0195196 | A1 | 8/2006 | Pendleton et al. |
| 2006/0229732 | A1 | 10/2006 | Bachelier |
| 2009/0082875 | A1 | 3/2009 | Long |
| 2010/0145461 | A1 | 6/2010 | Landry et al. |
| 2010/0217395 | A1 | 8/2010 | Bertagnoli et al. |

OTHER PUBLICATIONS

BioPro, Inc., information (downloaded Mar. 9, 2010): 1. A. "Great Toe Hemi Implant." B. Brochure entitled, "Hemi Implant." C. Brochure on surgical technique, entitled, "Metallic Hemiarthroplasty Resurfacing Prosthesis for the Hallux Metatarsophalangeal Joint," brochure No. 06053, ca. 1995. 2. A. "Modular Basal Thumb Implant." B. Brochure entitled, "Thumbs Up." C. Surgical technique brochure, "Modular Thumb Implant."
BioPro, Inc., brochure on surgical technique entitled, "PSL Physiological Stress Loading Total Hip Replacement System Utilizing the Horizontal Platform Supported Concept," Mar. 1998.
BioPro, Inc., brochure, "The BioPro Ceramic Tara," ca. Oct. 1997.
Brokenbrough, *Orthopedics Today*, Apr. 2005, p. 60.
Easley et al., *J. Am. Ac. Orthopaedic Surgeons*, vol. 10, No. 3, May/Jun. 2002, pp. 157-167.
Espinoza et al., "Misalignment of Total Ankle Components Can Induce High Joint Contact Pressures," an abstract of *J. Bone & Joint Surgery Am.*, vol. 92, No. 5, May 2010, pp. 1179-1187.
Gray, *Gray's Anatomy*, 1901 Ed., Barnes & Noble, 1995, p. 172.
Hintermann et al., American Academy of Orthopaedic Surgeons $72^{nd}$ Annual Meeting Instructional Course Lecture Handout, Feb. 23, 2005.
Lamb, *J. Bone & Jt. Surgery*, vol. 40B, No. 2, May 1958, pp. 240-243.
Pritchett, *Clin. Orthop. Relat. Res.*, vol. 466, "Curved-stem Hip Resurfacing, Minimum 20-year Followup," pp. 1177-1185, 2008.
Saltzman, *Orthopedics Today*, Round Table, Apr. 2005, pp. 64, 66, 68 and 70.
Signal Medical Corp., "SMC Great Toe," May 6, 2002, engineer drawing.
Smith, *Orthopedic Seminars*, University of Southern California Department of Orthopedic Surgery, 1972 vol. 5, Sep. 9, 1972, pp. 405-407.
Tornier, Inc., Salto Talaris™ Total Ankle Prosthesis, 2014.
Wright Medical, "Swanson Titanium Basal Thumb Implant," prior to 1999.
Wright Mfg. Co., "Smith Total Ankle," 1975, plus engineering prints from 1972.

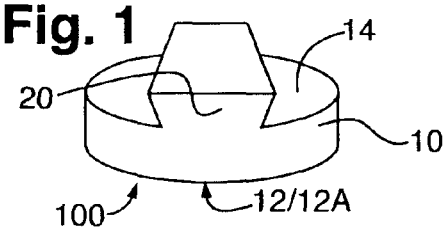
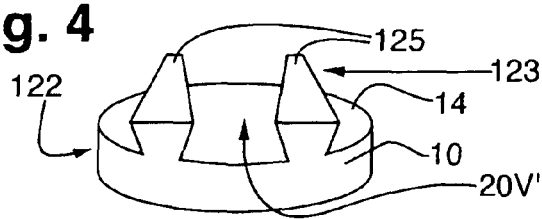
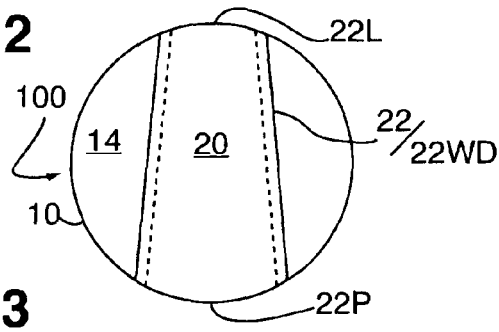
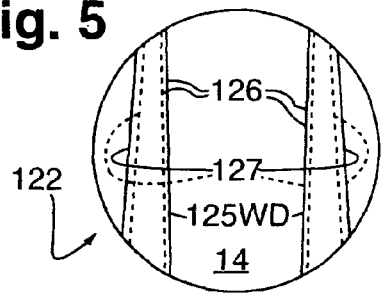
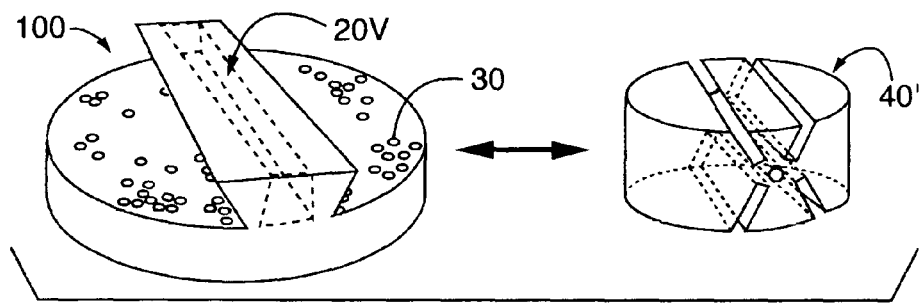
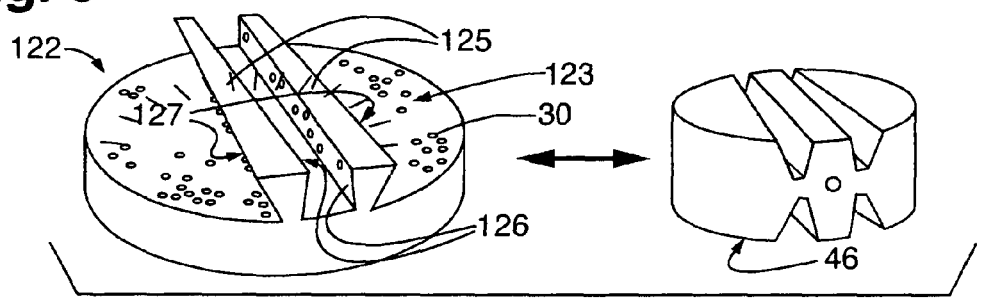
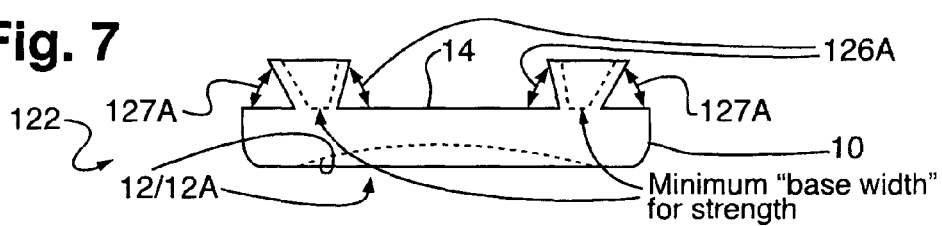

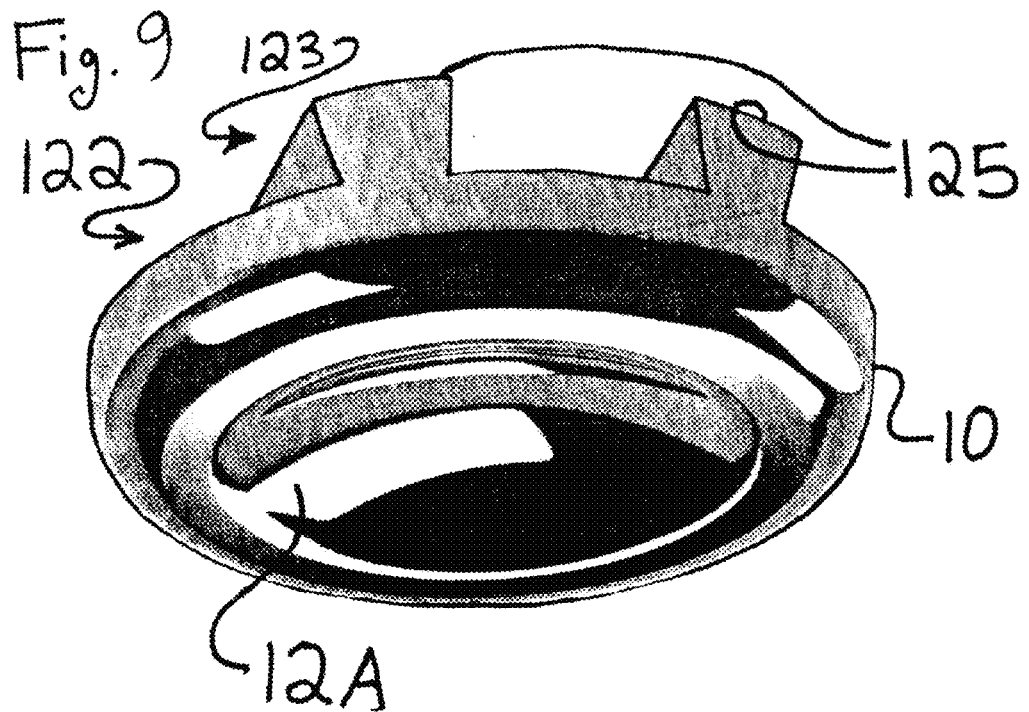
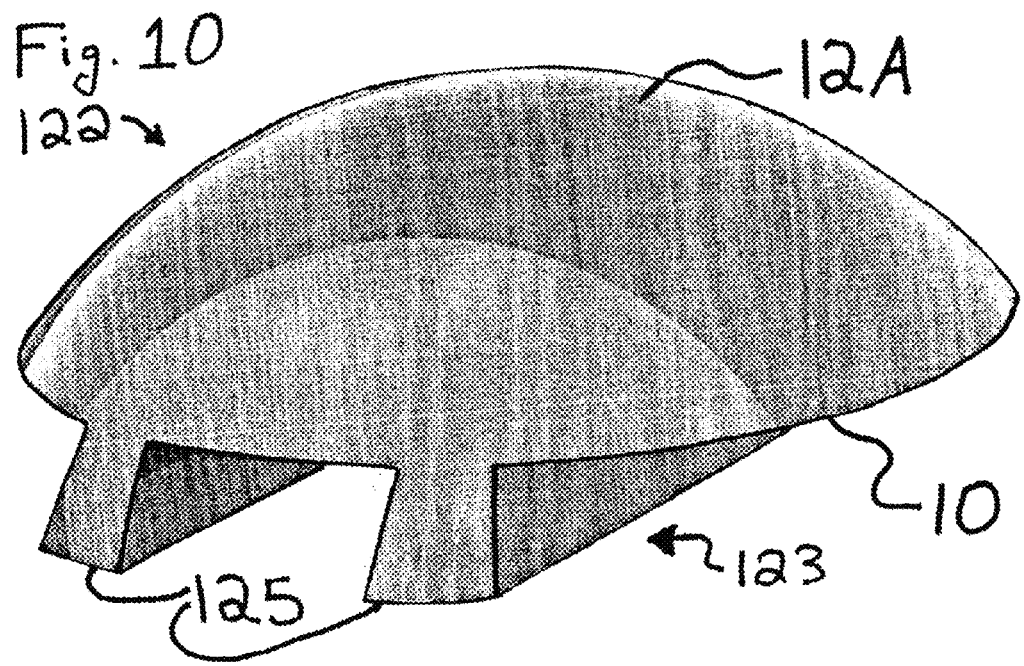

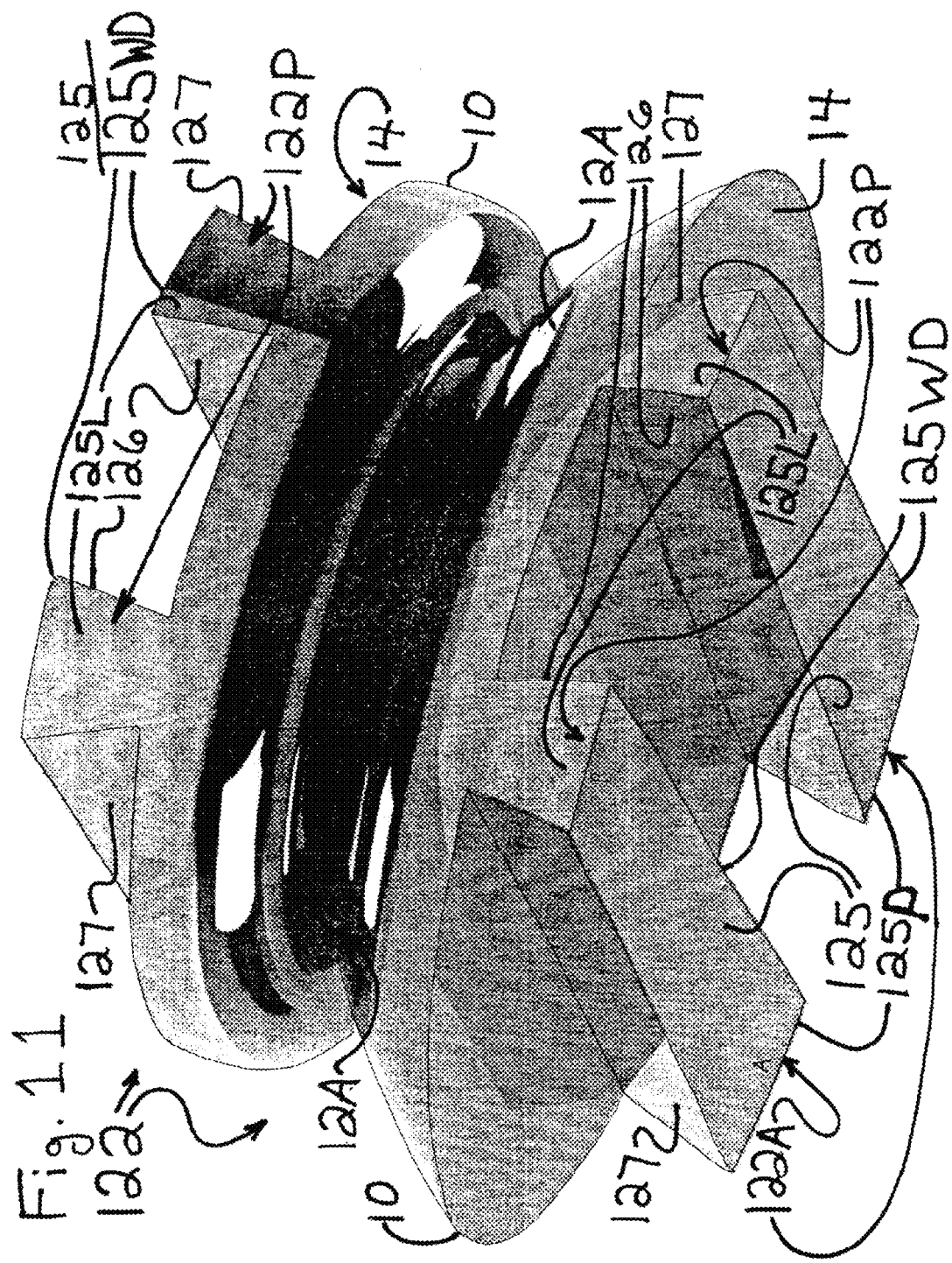

RAIL-FIXING IMPLANT

FIELD AND PURVIEW OF THE INVENTION

In general, this concerns a non-spinal vertebral, orthopedic implant or implant component device fixable transversely by a transverse rail stem system into resected bone. The device has a further utile feature away from the transverse rail system, for example, an articulation surface. Examples of the device can include those for an ankle, a digit, an elbow, a jaw, a kneecap, a knee, and so forth. The transverse rail system may be found, for example, as a pair of transverse rails. Each transverse rail may be in a form of a wedge, for example, a dovetail wedge. Of concern also are kits, for example, a kit containing the device, say, as a hemiarthroplasty or total joint arthroplasty implant, or an assortment of the devices in various sizes or of various materials, and associated surgical template(s) and possibly other tool(s) for preparing bone(s) for receipt of the device(s).

BACKGROUND TO THE INVENTION

The well-known Smith Total Ankle is a successful prosthetic implant. In such a cup and dome system, a tibial component has, for example, a stem (fin) that is inserted transversely, in an anterior to posterior direction, into a notch cut in the distal portion of the tibia. See, Wright Mfg. Co., "Smith Total Ankle," 1975, plus engineering prints from 1972. As fine as a provision as it is, a problem with such an arrangement is that in the insertion of the tibial component, force such as by pounding is employed, and the ankle component with its fin may be inadvertently pounded through and past its intended mark.

Smith et al., U.S. provisional patent application No. 60/998,198 filed on Oct. 9, 2007 A.D. and nonprovisional utility patent application Ser. No. 12/287,378 filed on Oct. 8, 2008 A.D., now U.S. Pat. No. 9,486,321 B1, address the foregoing. The specifications of those applications, i.e., the '198 and '378 applications, to include their drawings, are incorporated herein by reference in their entireties.

Art in addition to the foregoing cited in the incorporated '378 application includes the following:

Tronzo, U.S. Pat. No. 3,840,904 (Oct. 15, 1974) for acetabular cup prosthesis.

Smith, U.S. Pat. No. 3,889,300 (Jun. 17, 1975). This discloses an articulated two-part prosthesis replacing an ankle joint. Compare, Smith Total Ankle.

Freeman et al., U.S. Pat. No. 3,965,489 (Jun. 29, 1976). This discloses an endoprosthetic bone joint device for the talo-navicular joint.

Kinnett, U.S. Pat. No. 4,550,450 (Nov. 5, 1985). This discloses a total shoulder prosthesis system.

Epinette, U.S. Pat. No. 4,743,261 (May 10, 1998). This discloses a trial component for a unicompartmental knee prosthesis for cementless implantation.

Tronzo, U.S. Pat. No. 4,743,262 (May 10, 1988) with re-examination certificate B1 4,743,262. This discloses an acetabular cup prosthesis.

Hofmann, U.S. Pat. No. 4,936,863 (Jan. 26, 1990). This discloses a hip prosthesis Cremascoli, U.S. Pat. No. 4,957,510 (Sep. 18, 1990). This discloses a hip prosthesis structure adapted for easy fitting to the patent coxo-femural articulation.

Bekki et al., U.S. Pat. No. 5,007,932 (Apr. 16, 1991). This discloses an artificial bone joint.

Koenig, U.S. Pat. No. 5,037,440 (Aug. 6, 1991). This discloses an orthopedic toe joint implant.

Saffar, U.S. Pat. No. 5,047,059 (Sep. 10, 1991). This discloses a prosthesis for metacarpoealangeal or interphalangeal articulation of the fingers.

Zang et al., U.S. Pat. No. 5,314,486 (May 24, 1994). This discloses a non-constrained total joint system.

Whipple et al., U.S. Pat. No. 5,702,469 (Dec. 30, 1997). This discloses a thumb joint prosthesis and related method of implantation.

Kummer et al., U.S. Pat. No. 5,910,171 (Jun. 6, 1999). This discloses components for modular shoulder and hip prostheses.

Huebner, U.S. Pat. No. 6,102,953 (Aug. 15, 2000). This discloses a shoulder prosthesis.

Townley, U.S. Pat. No. 6,299,647 B1 (Oct. 9, 2001). This discloses a snap-fitting, non-dislocating hip joint socket implant.

Tornier, U.S. Pat. No. 6,454,809 B1 (Sep. 24, 2002). This discloses a modular acetabular or cotyloid implant.

Lester et al., U.S. Pat. No. 7,476,255 B1 (Jan. 13, 2009). This discloses a soft tissue attachment system and method.

Burstein et al., Pub No. US 2002/0055784 A1 (May 9, 2002). This discloses composite bearing inserts for total knee joints.

Eisermann et al., Pub. No. US 2003/0208273 A1 (Nov. 6, 2003). This discloses an intervertebral prosthetic joint.

Nicholson et al., Pub. No. US 2003/0233147 A1 (Dec. 18, 2003). This discloses a device for spinal fusion.

Luchesi et al., Pub. No. US 2004/0167631 A1 (Aug. 26, 2004). This discloses a fixation surface for an ankle prosthesis.

Hazebrouck, Pub. No. US 2004/0193268 A1 (Sep. 30, 2004). This discloses an intercalary prostheses, kit and method.

Lester et al., Pub. No. US 2005/0143834 A1 (Jun. 30, 2005). This discloses a soft tissue attachment system and method. Note, the '255 patent.

Serafin, Jr. et al., Pub. No. US 2006/0025866 A1 (Feb. 2, 2006). This discloses ceramic manufactures. Note, paragraph No. 0144; FIGS. 59-64 (ceramic ankle joint ensemble); and so forth.

Pendleton et al., Pub. No. US 2006/0195196 A1 (Aug. 31, 2006). This discloses a modular trial implant with a mortise coupling.

Bachelier, Pub. No. US 2006/0229732 A1 (Oct. 12, 2006). This discloses a femoral prosthesis component.

Long, Pub. No. US 2009/0082875 A1 (Mar. 26, 2009). This discloses a talar implant system and method.

Bertagnoli et al., Pub. No. US 2010/0217395 A1 (Aug. 26, 2010). This discloses an intervertebral implant with a keel.

Landry et al., Pub. No. US 2010/0145461 A1 (Jun. 10, 2010). This discloses instrumentation and a procedure for implanting spinal implant devices.

Benoist, Pub. No. EP 1 707 157 A1 (Oct. 4, 2006). This is corresponds to the Bachelier US '732 publication.

Serafin, Jr. et al., WO 2004/0830 A2 (Sep. 23, 2004). This discloses ceramic manufactures and is the Serafin, Jr. et al. US '866 publication parent.

BioPro, Inc., information (downloaded Mar. 9, 2010):
1. A. "Great Toe Hemi Implant."
   B. Brochure entitled, "Hemi Implant."
   C. Brochure on surgical technique, entitled, "Metallic Hemiarthroplasty Resurfacing Prosthesis for the Hallux Metatarsophalangeal Joint," brochure No. 06053, ca. 1995.
2. A. "Modular Basal Thumb Implant."
   B. Brochure entitled, "Thumbs Up."
   C. Surgical technique brochure, "Modular Thumb Implant."
BioPro, Inc., brochure on surgical technique entitled, "PSL Physiological Stress Loading Total Hip Replacement System Utilizing the Horizontal Platform Supported Concept," March 1998.
BioPro, Inc., brochure entitled, "The BioPro Ceramic Tara," ca. October 1997.
Brokenbrough, *Orthopedics Today*, April 2005, page 60. This reports on decreased pain, but a 25% complication rate with the DuPuy Agility total ankle replacement (TAR).
Easley et al., *J Am. Ac. Orthopaedic Surgeons*, Vol. 10, No. 3, May/June 2002, pages 157-167. This reports on total ankle arthroplasty.
Espinoza et al., "Misalignment of Total Ankle Components Can Induce High Joint Contact Pressures." This is an abstract of *J. Bone & Joint Surgery Am.*, Vol. 92, No. 5, May 2010, pages 1179-1187.
Gray, *Gray's Anatomy*, 1901 Ed., Barnes & Noble, 1995, page 172. This illustrates and identifies bones of the right foot.
Hintermann et al., American Academy of Orthopaedic Surgeons 72$^{nd}$ Annual Meeting Instructional Course Lecture Handout, Feb. 23, 2005. This reports on then current state of the art for total ankle arthroplasty.
Lamb, J. *Bone & Jt. Surgery*, Vol. 40B, No. 2, May 1958, pages 240-243. This reports on the ball and socket ankle joint, a congenital abnormality.
Pritchett, *Clin. Orthop. Relat. Res.*, Vol. 466, "Curved-stem Hip Resurfacing, Minimum 20-year Followup," pages 1177-1185, 2008.
Saltzman, *Orthopedics Today, Round Table*, April 2005, pages 64, 66, 68 and 70. This reports on ankle fusion and total ankle replacement, making the right choices, how top physicians make the call.
Signal Medical Corp., "SMC Great Toe," May 6, 2002, engineering drawing.
Smith, *Orthopedic Seminars*, University of Southern California Department of Orthopedic Surgery, 1972 Vol. 5, Sep. 9, 1972, pages 405-407. This reports on total ankle replacement, a case presentation.
Tornier, Inc., "Salto Talaris™ Total Ankle Prosthesis, 2014.
Wright Medical, "Swanson Titanium. Basal Thumb Implant," prior to 1999.

Needs and Desires

As good as the foregoing may be, particularly that of the Smith Total Ankle and Smith '300 patent, and the incorporated '198 and '378 applications, the art is in need of advancements and improvements. It would be desirable, in turn, to further ameliorate or even more completely overcome any drawback, and provide the art further alternative(s).

Foundations as Related to the Incorporated '378 Application

In general, the incorporated '378 application may be considered to provide an implant or implant component device comprising a load-bearing implant or component therefor, which bears load substantially in a load-bearing direction when implanted, and which includes at least one implant body, each having connected thereto one and only one transverse stem, which runs in a first transverse direction substantially perpendicular to the load-bearing direction, and which has along the first transverse direction a leading element and a pursuing element—with the leading element having and terminating in a leading element wall projecting from the at least one implant body, which has a lateral or radial dimension along a second transverse direction essentially perpendicular to the first transverse direction and substantially perpendicular to the load-bearing direction that is less than that of the pursuing element; with the pursuing element having and originating in a pursuing element wall projecting from the at least one implant body, which has a lateral or radial dimension along said second transverse direction but spaced apart from the leading element wall; and with each of the leading and pursuing element walls projecting in its entirety substantially perpendicular from the pertinent at least one implant body—which one and only one transverse stem has between the leading and pursuing elements two spaced apart outside side walls projecting from the at least one implant body, with each of the leading and pursuing element walls separately connecting with the two spaced apart outside side walls. The leading element wall is not greater than a lateral or radial distance between the two spaced apart outside side walls about the leading element; and the pursuing element wall is not substantially greater than a lateral or radial distance between the two spaced apart outside side walls about the pursuing element. The one and only one transverse stem is adapted for transverse insertion into resected bone configured for complementary female reception of the one and only one transverse stem such that the one and only one transverse stem has a laterally disposed feature for providing stopping of the one and only one transverse stem along a path it takes in its transverse insertion into said bone. On the at least one implant body, away from and generally opposing the one transverse stem, can be a surface for articulation.

As well, in general, the incorporated '378 application may be considered to provide an implant device for insertion in a joint having confronting first and second bones, which includes an implant body having a substrate-interfacing element and, on an opposite side of the body but not confronting said element, a working surface configured to face the second bone and to be disposed in a predetermined position relative to the first bone when implanted; and a transversely elongated stem on the body having leading and pursuing ends for implantation in an elongated, resected passage of the first bone when the elongated, resected passage of the first bone projects in a direction transverse to an axis generally perpendicular to the confrontation of the first and second bones; has respective first and second ends, at least the first end being open; has two opposing lateral walls, at least one lateral wall of which with a surface facing the first end to provide a laterally disposed feature for providing stopping of a transversely elongated stem having leading and pursuing ends inserted therein, with the leading end thinner laterally than the pursuing end; and optionally, projects in an anterior to posterior direction. Therein, the stem is configured to complementarily fit the resected passage in the first bone, and includes two opposing side walls for respectively engaging the two lateral walls of the elongated, resected passage, with at least one side wall of the two opposing side walls that can engage the aforesaid at least one lateral wall of the elongated, resected passage of the first bone to provide for stopping of the stem therein and to maintain the working surface in a predetermined position when the stem is inserted into the elongated, resected passage of the first bone from the first end thereof and the working surface is positioned in the predetermined position; the leading and pursuing ends of the stem are each in a form of a wall that projects in its entirety substantially perpendicular from the substrate-engaging element; the leading end of the stem is thinner laterally than the pursuing end of the stem; the two opposing side walls of the stem angle laterally outwardly away from one another from a first location by the implant body to a second location spaced apart from the implant body so as to form a first tapered dovetail configuration; and the stem is configured to angle the two opposing side walls from the leading end to the pursuing end laterally outwardly away from one another at an angle about from 1 to 10 degrees.

Also, the incorporated '378 application provides, among other implants, a certain ankle implant.

And, the incorporated '378 application provides a certain kit. It can include a joint prosthesis with a tool.

A More Full Disclosure of the Invention

Provided hereby, in general, is—in the aforementioned foundation of the implant or implant component device comprising a load-bearing implant or component therefor—the improvement which comprises a void volume spanning from the leading element to the pursuing element and running in the first transverse direction substantially perpendicular to the load-bearing direction substantially having laterally in the second transverse direction essentially perpendicular to the first transverse direction and substantially perpendicular to the load-bearing direction a plurality of opposing inner walls, so as to form from the one and only one transverse stem a transverse rail stem system including a plurality of separate transverse rails, each transverse rail having a rail leading element and a rail pursuing element. The transverse rail stem system is adapted for insertion into resected bone configured for complementary female reception of the transverse rail stem system such that the transverse rail stem system has a laterally disposed feature for providing lateral stopping of the transverse rail stem system after insertion into said bone. In general, however, the at least one implant body is not one which is adapted for arthroplasty of opposing spinal vertebrae such that the implant or implant component device is not a spinal vertebral implant.

As well, provided hereby, in general, is—in the aforementioned foundation of the implant device for insertion in a joint having confronting first and second bones—the improvement which comprises, in addition to the transversely elongated stem, which is designated a first transversely elongated stem, provision of a second transversely elongated stem, which is spaced apart from the first transversely elongated stem so as to form a transverse rail stem system including a plurality of separate transverse rails, wherein the second transverse stem has second transverse stem leading and pursuing ends for implantation in a second elongated, resected passage of the first bone when the second elongated, resected passage of the first bone projects in a direction transverse to the axis generally perpendicular to the confrontation of the first and second bones; has respective third and fourth ends, at least the third end being open; has two opposing lateral walls; and, optionally, projects in an anterior to posterior direction. Therein, the second transverse stem is configured to complementarily fit the second elongated, resected passage in the first bone, and includes two opposing second transverse stem side walls for respectively engaging the two lateral walls of the second elongated, resected passage in the first bone for maintaining the working surface in the predetermined position when the second transverse stem is inserted into the second elongated, resected passage of the first bone from the third end and the working surface is positioned in the predetermined position. In general, however, the implant body is not one which is adapted for arthroplasty of opposing spinal vertebrae such that the implant device is not a spinal vertebral implant.

Also, provided hereby, in general, is an ankle arthroplasty implant device. In one embodiment, it can comprise first and second implant bodies for implanting in respective talar and tibial bones of a patient, the first body including a truncated, convex spherically shaped dome articular surface, and the second body including a truncated, concave spherically shaped socket articular surface for operatively engaging with said dome; and first and second transversely elongated wedge-shaped stems on the first implant body and third and fourth transversely elongated wedge-shaped stems on the second implant body, each of said first, second, third and fourth wedge-shaped stems having leading and pursuing ends, each of which has one and only one wall projecting from its respective body and in its entirety substantially orthogonal thereto at an outer boundary of said body, and including respective spaced apart side walls angling laterally outwardly away from one another from the respective leading toward the pursuing ends to form respective dovetail configurations.

And, provided hereby, in general, is a kit. In one embodiment, it is a combination comprising, in kit form. For example, an element of the kit can be a joint prosthesis apparatus for implant at a selected transverse location in an articulating, weight bearing joint space presenting male and female joint components, the joint components having a predetermined transverse width and being formed with respective through, elongated wedge shaped, dovetail, transverse resection channels located at selected positions in the respective joint components and being of a predetermined shape, having opposite dovetail sides converging linearly along their lengths at a selected angle with respect to one another in the transverse direction from respective wide channel openings formed to open to the respective one transverse side of the joint and narrower channel openings formed to open on the transverse side of the joint opposite the one transverse side, the joint prosthesis apparatus including prosthesis devices to implant in the articulating joint space, each of these having a body with a substrate-interfacing element, with a first of the devices including a truncated concave sphere shaped socket and a second of the devices including a truncated convex sphere shaped ball element to be received complementarily in the socket, wherein the substrate-interfacing element in the first of these devices is opposite but not confronting the socket and the substrate-interfacing element in the second of these devices is opposite but not confronting the ball element. Each of the prosthesis devices includes a pair of axial stems, each stem configured with opposite dovetail shaped stem side walls diverging linearly away from one another at the selected angle in a transverse wedge shape with a narrow leading end and a wide trailing end and constructed to be received transversely from the respective wide channel openings to be nested in close fit relationship in the respective resection channel to wedge against the side walls of the resected channels located at the selected location such that a surgeon can extend a bone-resecting instrument fully through in the lateral direction across the joint components to form the resection channels with channel side walls angling toward one another at the selected angle to define the predetermined shape in the joint components; and the devices are selected and the stems are introduced through the wide openings of the respective channels to be driven transversely into the channels from the wide channel openings to wedge the stems in close fit relationship in the respective channels at the selected location. Another element of the kit can be at least one template tool to be disposed adjacent the joint components, wherein the at least one template tool includes a tool body in substantially thick disc form having a first surface, a second surface opposing but not confronting the first surface, and an outer wall boundary connecting the first and second surfaces. The tool body is constructed with a pair of guide grooves diverging away from one another at the selected angles, each guide groove passing through the first surface and, at two locations, the outer wall boundary, and configured and oriented to receive the bone-resecting instrument to project therefrom to form transverse resection channels for at least one of the joint components for receipt of one of the prosthesis devices configured with the predetermined shape.

The invention is useful in arthroplasty.

By the invention, the art is advanced and improved in kind, with drawbacks in the art further ameliorated or even more completely overcome, and further alternatives are provided. In general, a plurality of transverse rails or stems is provided with respect to a body of an implant or implant component. For example, a pair of transverse rails or stems, which can be oriented to lie substantially along the same axis or direction. One or more of the stems or rails may be in a form of a wedge, for example, a dovetail wedge. Beneficially, patient bone can be conserved to an even greater extent, and surgical implantation can be carried out more easily. In addition, more surface area of bone is available for contact with more surface area of the implant, which can improve, among other things, stability, reliability, and longevity of the implant. Fewer specialized tools are required for effective implantation. Surgery is made easier, with surgical time able to be reduced and surgical reliability able to be increased. Surgical cement may be avoided. Patient recovery and mobility can be enhanced. Implants and tools of the invention can be efficiently manufactured.

Numerous further advantages attend the invention.

The drawings form part of the specification hereof With respect to the drawings, which are not necessarily drawn to scale, the following is briefly noted:

FIG. 1 is a perspective view of an exemplary embodiment of a wedge-fixing implant from the incorporated '198 and '378 applications such as a tibial component for an ankle.

FIG. 2 is a top (proximal to distal) plan view of the implant of FIG. 1.

FIG. 3 is a perspective plan view of a wedge-fixing implant generally such as that of FIG. 1 depicting material that may be removed from the implant such that a rail-fixing implant can be provided, accompanied by a surgical template. This may comprise a kit.

FIG. 4 is a perspective view of an exemplary embodiment of a rail-fixing implant such as a tibial component for an ankle.

FIG. 5 is a top (proximal to distal) plan view of the implant of FIG. 4.

FIG. 6 is a perspective view of a rail-fixing implant generally such as the implant of FIG. 4, accompanied by a surgical template. This may comprise a kit. Compare with FIG. 3.

FIG. 7 is a side plan view of a rail-fixing implant such as of FIG. 4.

Figure 8:
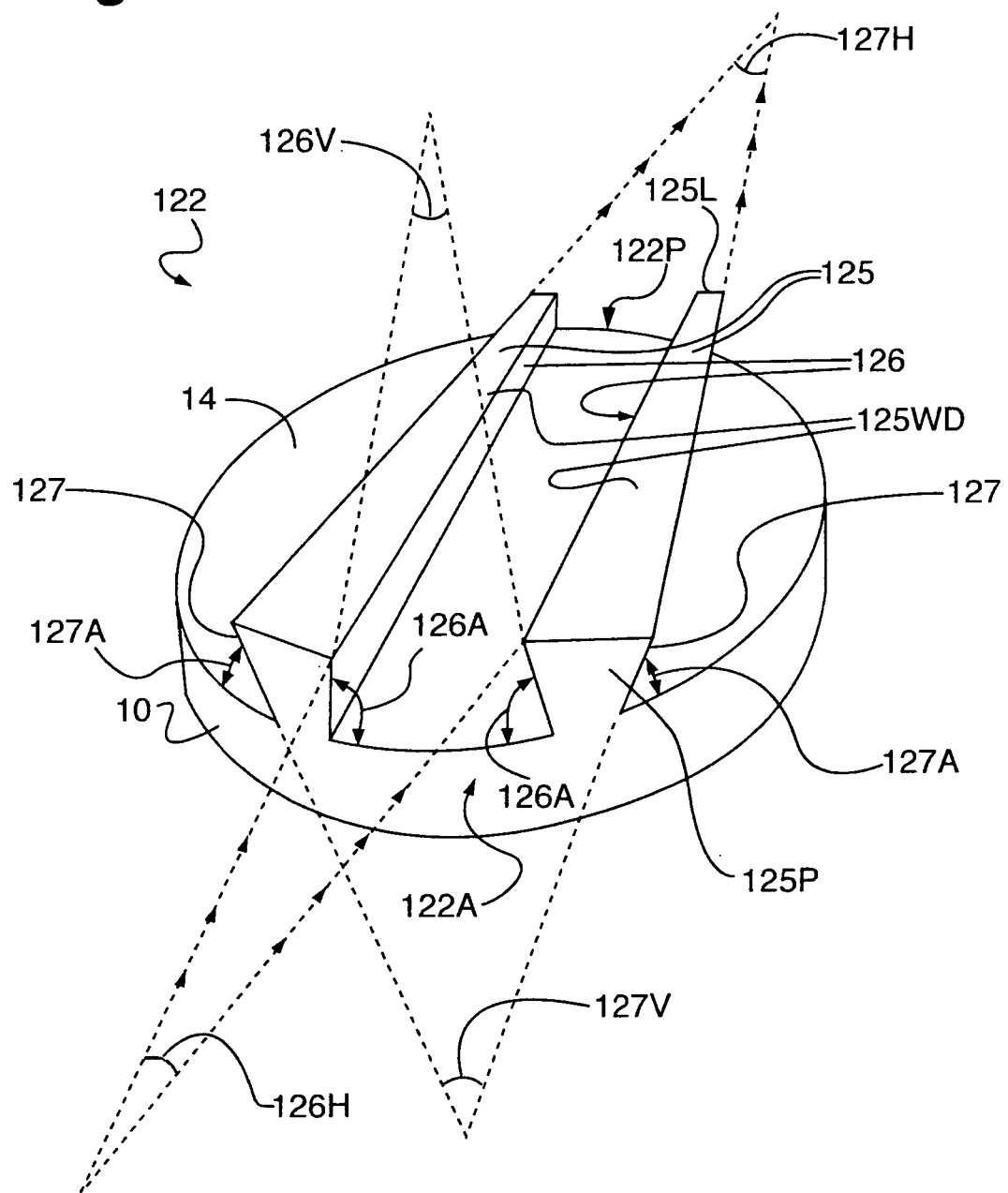

FIG. 8 is a perspective view of a rail fixing implant such as of FIG. 4, which designates various angles.

FIG. 9 is a perspective view of a rail-fixing ankle implant, tibial component.

FIG. 10 is a perspective view of a rail-fixing ankle implant, talar component.

FIG. 11 is a perspective view, generally in a posterior-to-anterior direction, of the tibial and talar components of FIGS. 9 and 10, an ensemble, assembled.

Figure 12:
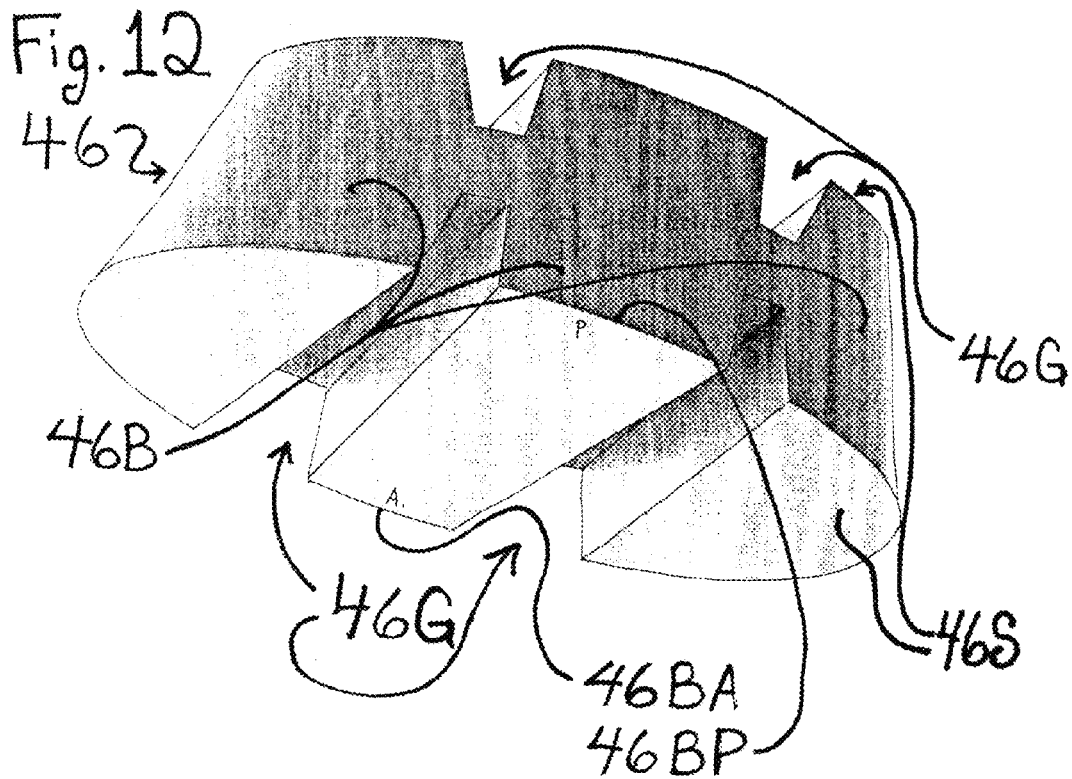

FIG. 12 is a perspective view, generally in a posterior-to-anterior direction, of a bone preparation/cutting template for implantation of a total rail-fixing ankle implant such as of FIG. 11.

Figure 13:
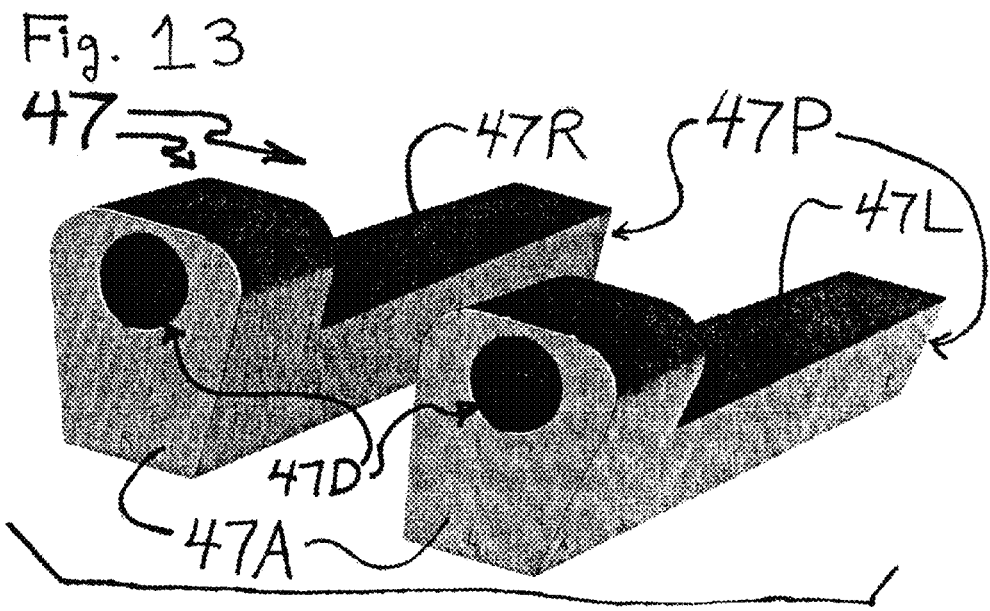

FIG. 13 is perspective view, generally in an anterior-to-posterior direction, of right and left (from a patient's perspective) drill guides to assist in surgical implantation of an implant such as of FIG. 11 in conjunction with a template as of FIG. 12.

Figure 14:
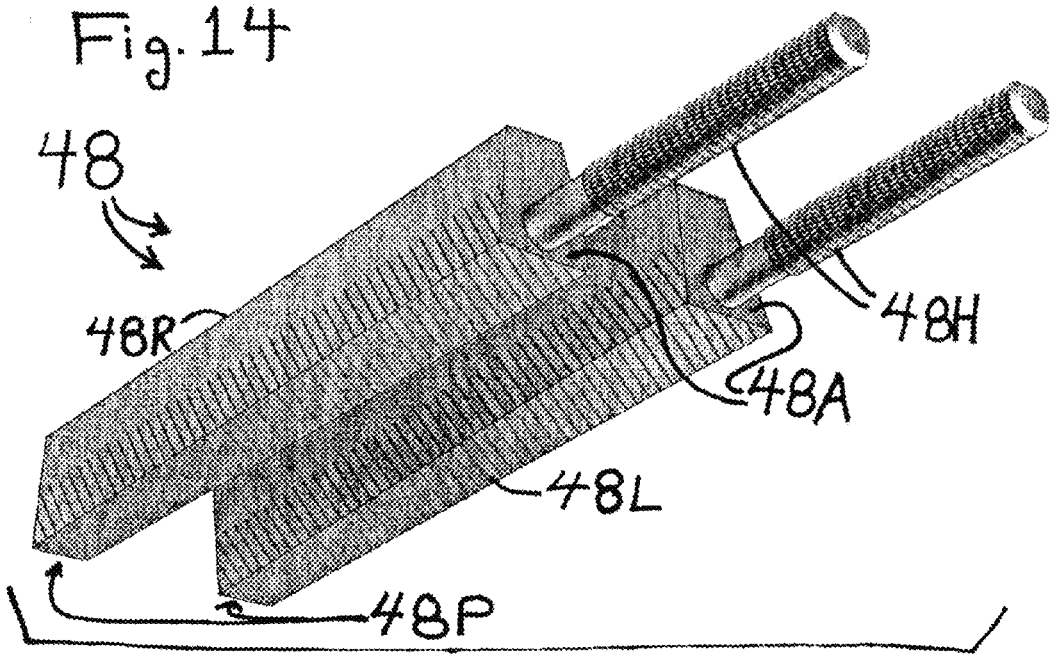

FIG. 14 is a perspective view, generally in an anterior-to-posterior direction, of right and left (from a patient's perspective) broaches to assist in surgical implantation of an implant such as of FIG. 11 in conjunction with a template such as of FIG. 12.

Figure 15:
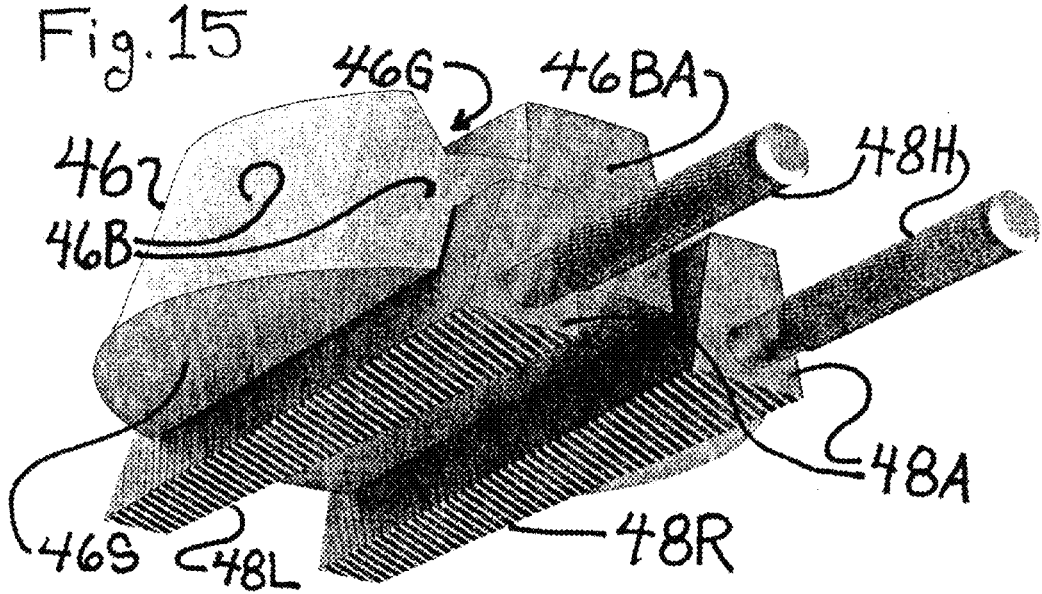
Figure 16:
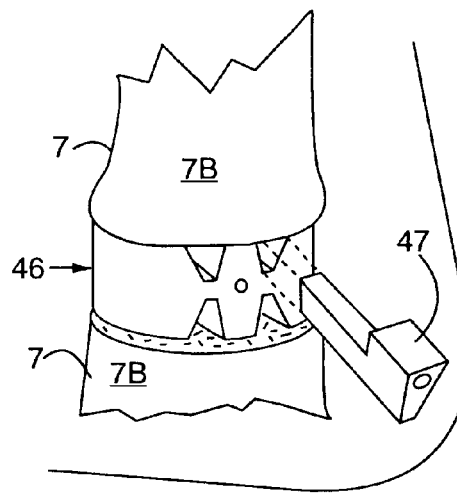
Figure 17:
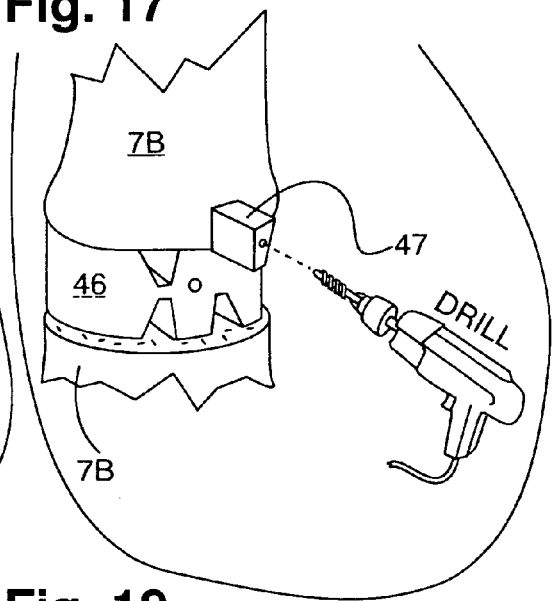
Figure 18:
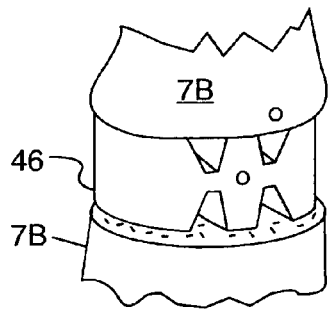
Figure 19:
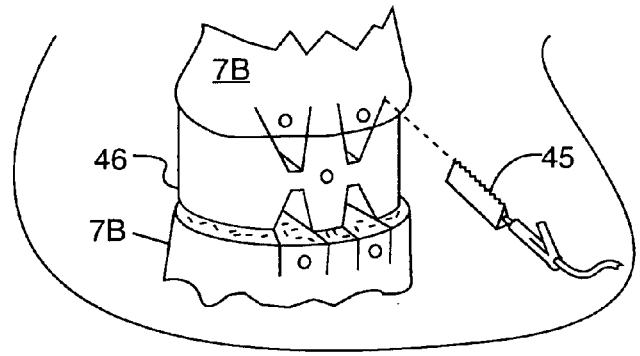
Figure 20:
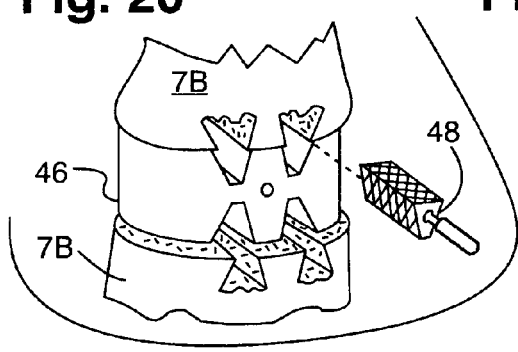
Figure 21:
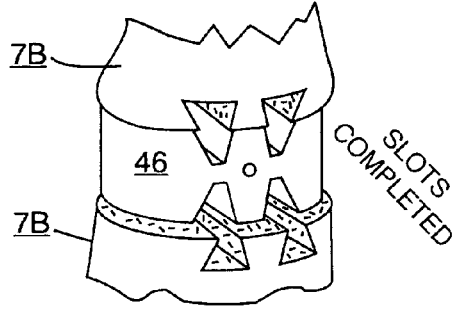

FIG. 15 is a perspective view, generally in an anterior-to-posterior direction, of the template of FIG. 12 into which are positioned the right and left broaches of FIG. 14.

FIGS. 16-24 are perspective plan views illustrating, generally as in a sequence, implantation of a rail-fixing total ankle implant such as found within FIGS. 4-11, with tools therefor to include as found within FIGS. 12-15. The sequence may be varied.

Figure 25:
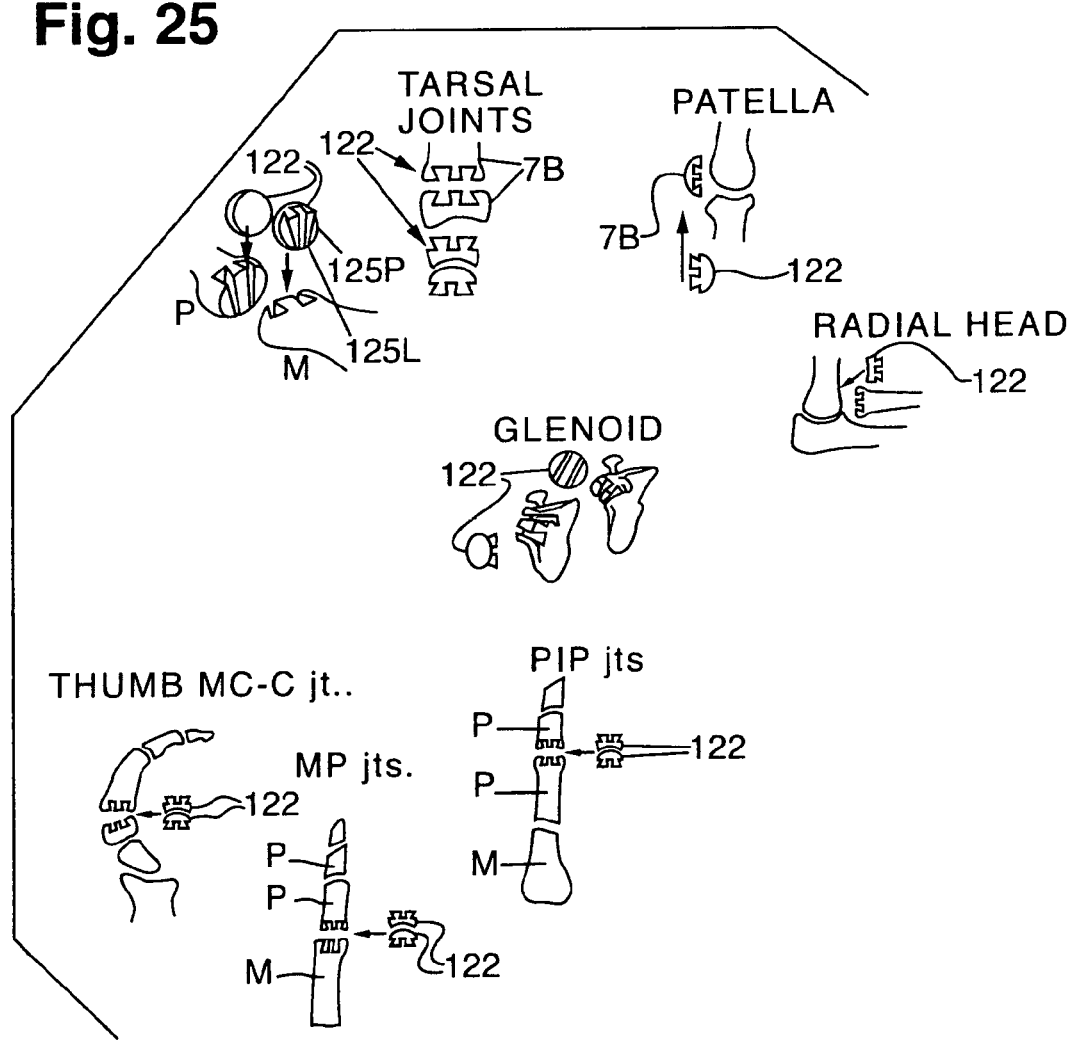

FIG. 25 denotes various further rail-fixing implants hereof.

The invention can be further understood by the detail set forth below. As with the foregoing, the following, which also may be read in view of the drawings, should be taken in an illustrative and not necessarily limiting sense:

The present rail-fixing implant includes an implant body with a working surface, for example, a smooth articulating surface, and, away from the articulating surface, a transverse rail stem system. The transverse rail system is configured with a plurality of transverse rails or stems, one or all of which can be wedge-shaped, for example, as dovetail-shaped wedge(s). The transverse rails or stems run generally parallel with one another for transverse insertion into a substrate, for example, resected bone formed to include grooves into which the rails or stems fit. Advantageously, at least two of the transverse rails or stems are wedge-shaped, for example, as a pair of dovetail-shaped wedges. Thereby, lateral stopping of the implant can be conveniently effected. In addition, with the dovetail-shaped wedges, plumb holding can be provided or enhanced.

Surgical tools can enhance ease and reliability of implantation of the rail-fixing implant. Among such tools can a template, which has precisely positioned grooves for insertion and control of bone-preparing tools such as a saw or even more advantageously a precisely configured broach or plural set broaches. Drill guide(s) and/or broach(es) can be provided so as to assist in more effective and precise bone removal and so forth.

The rail-fixing implant or implant component and tools for surgical implantation of the same can be made of any suitable material(s). For instance, the implant or implant component, or a part thereof, may be made of a metal such as a cobalt-chrome alloy, a stainless steel, or a titanium alloy; a ceramic such as an alumina and/or a zirconia, particularly a magnesium oxide stabilized zirconia, for example, a magnesium oxide stabilized transformation toughened (which may also be referred to as tetragonally toughened) zirconia; and/or a composite or a plastic material such as a fiber composite, an ultra high molecular weight polyurethane, a nylon, or a polyurethane. Likewise, the tools, to include templates, may be made of a suitable metal, ceramic and/or composite or plastic material. Metal implants may be advantageously provided.

Methods known in the art can be employed to make the implant and tools. Thus, for instance, as known to skilled artisans, among various techniques, a metal implant, or implant component or part thereof can be made such as by casting, forging or machining, and polishing; ceramic, such as by machining, firing, and polishing; and composite or plastic material such as by molding and/or machining. A rough or porous coating such as for enhanced bone-ingrowth may be provided such as by molding, machining, vapor deposition, plasma spraying, and so forth. The tools may be made similarly. Other suitable techniques may be employed.

With more particular reference to the drawings, wedge-fixing implant 100 is compared with rail-fixing implant 122. The implants 100 and 122 can be adapted for implantation in bodily substrate 7, for example, human bone 7B; can be of the load bearing type such as for an articulating joint or other body subsystem, typically not a spine; and include implant body 10. But, whereas the implant 100 has fin type stem 20 connected to the body 10 and adapted for transverse insertion into the substrate 7/7B, the implant 122 has transverse rail stem system 123 with plurality of rails 125 connected to the body 10 and adapted for transverse insertion into the substrate 7/7B.

The body 10 of the implants 100 and 122 may have connected thereto, spaced apart from the transverse stem 20 of the implant 100 or the transverse rail stem system 123 of the implant 122, further utile feature 12, for example, smooth articulation surface 12A. For example, in a total ankle joint implant, the smooth articulation surface 12A of the tibial component can be a concave portion of an internal outer surface of a sphere with the smooth articulation surface 12A of the talar component an appropriately corresponding convex portion of an external outer surface of a sphere. Substrate-interfacing element 14 may be present, depending on the configuration of the implant, away from, so as not to interfere with any operation of, the further utile feature 12. Securing pin receiving hole 15, which may include threads, may be provided.

The transverse stem 20 may have enough volume 20V such as for a comparison with, or be designated for removal so as to form, void volume 20V between the rails 125 of the transverse rail system 123 of the rail-fixing implant 122. Be that as it may, the transverse stem 20, includes laterally disposed feature 22, which has leading element 22L with a lateral dimension thinner than that of pursuing element 22P that trails the leading element 22L in insertion of the wedge-fixing implant 100 into the substrate 7/7B. The laterally disposed features 22 may be provided in a form of a wedge, especially dovetail-shaped wedge 22WD, which provides at least lateral holding force in the substrate 7/7B with the dovetail-shaped wedge 22WD providing not only lateral holding force but also plumb holding force, i.e., in general, force orthogonal to the plane of the lateral holding force, in the substrate 7/7B, particularly through its intrinsically provided "overhang." By the laterally disposed feature 22, which would include the dovetail-shaped wedge 22WD, the stem 20 can be intrinsically stopped in the path it takes in its insertion into the substrate 7/7B, notably in a desired location. As well, through the transverse stem 20, the wedge-fixing implant 100 can be held in place thereby.

The rail-fixing implant 122 such as, for example, when embodied as an implant for a dysfunctional ankle joint, may have anterior (front) portion 122A and posterior (back) portion 122P. Typically, with respect to implantation, these would be oriented toward the front and back of the patient, respectively.

The transverse rail stem system 123 includes a plurality, for example, a pair, of transverse rails 125; each may have leading element 125L and pursuing element 125P. A transverse rail 125 may have a leading element 125L with a lateral dimension thinner than that of a corresponding pursuing element 125P, which trails the leading element 125L in insertion of the rail-fixing implant 122 into the substrate 7/7B; thus, such a transverse rail 125 is provided in a form of a wedge. Advantageously, however, at least one, and even more advantageously each transverse rail 125 is provided in a form of a dovetail wedge 125WD. Rail opposing, e.g., inner, walls 126, and rail opposing, e.g., outer, walls 127 may be found with the transverse rails 125—which may be oriented, for example, with reference to FIG. 8, according to angles such as follows:

| Angle | Comment |
| --- | --- |
| 126A | Angle in relation to a generally flat substrate interfacing surface 14, about from 45°, 60° or 80° to 87½° or 90°, say, about 85°. |
| 126H | Angle in transverse direction substantially perpendicular to load-bearing direction, about from 1°, 2° or 3° to 5°, 7° or 10°, say, about 4°. |
| 126V | Vertically oriented angle = 180° − (first 126A angle in degrees + opposing, second 126A angle in degrees), say, about 10°. |
| 127A | Angle in relation to a generally flat substrate interfacing surface 14, about from 45°, 75° or 80° to 85° or 90°, say, about 60°. |
| 127H | Angle in transverse direction substantially perpendicular to load-bearing direction, about from 1°, 2° or 3° to 5°, 7° or 10°, say, about 4°. |
| 127V | Vertically oriented angle = 180° − (first 127A angle in degrees + opposing, second 127A angle in degrees), say, about 60°. |

Each angle 126A in a corresponding 126A-126A pair may be or equal to or unequal with one another, say, equal; and each angle 127A in a corresponding 127A-127a pair may be equal to or unequal with one another, say, equal. Thus, with respect to the same transverse rail 125, the angle 126A may be greater, i.e., in general, have a more vertical orientation with respect to the substrate-interfacing element 14, than the angle 127A. Furthermore, each component for a total joint prosthesis may be provided with a transverse rail stem system 123 having transverse rails 125 defining the same angles 126A, 126H, 126V, 127A, 127H and 127V and perhaps dimensions in general as found in the corresponding component as may be applicable to the joint under consideration, say, the human ankle.

Rough or porous coating 30 may be provided all or part of the substrate-interfacing element 14 and/or stem 20 or transverse rail stem system 123. As is known in the art, the coating 30 in general can engender ingrowth of bony and/or fibrous tissue. Although it may be avoided in appropriate cases, surgical cement such as polymethylmethacrylate may be employed.

Thus, the rail-fixing implant 122 is provided in addition to the wedge-fixing implant 100. See, e.g., FIGS. 1-11 and 23-25.

As is the case with the wedge-fixing implant 100, the rail-fixing implant 122 can be implanted by those of skill in the surgical art, and any suitable method or process may be employed to carry this out. Thus, the wedge-fixing implant 100 can be implanted readily with the aid of various surgical tools, which can include bone-cutting template 40' and saw 45, and so forth; but, in general, the rail-fixing implant 122 can be implanted even more readily with the aid of various surgical tools, to include those specially configured for the purpose. And so, template 46 can include template body 46B having template body anterior portion 46BA, template body posterior portion 46BP, precisely configured grooves 46G, and substrate, e.g., bone, facing surfaces 46S. Drill guide 47 corresponding to and for properly orienting a groove 46G can be provided to include drill guide anterior portion 47A, about which is a member having drill bit accommodating hole 47D, and drill guide posterior portion 47P. Left and right side drill guides 47L and 47R, respectively, can correspond with left and right hand sides of the template 46 and patient. Broach 48 corresponding to and for entry within a groove 46G can be provided to include broach anterior portion 48A, protruding from which can be broach handle 48H, and broach posterior portion 48P. Left and right hand configured broaches 48L and 48R can be provided for correspondence in the template 46 with left and right hand side portions of the patient with respect to the site of implantation. See, e.g., FIGS. 12-24. The sequence of FIG. 16 et seq. may be varied. For example, sawing may initiate the formation of the grooves, followed by drilling to clear out a swath between saw cuts, followed by broaching to complete the grooves.

Herein, values and dimensions can be considered approximate or exact.

Thus, to recapitulate, the present rail-fixing implant includes a body and a utile feature, for example, a smooth articulating surface. This rail-fixing implant also includes a transverse rail stem system with a plurality of rails, spaced apart from the utile feature, which is adapted for transverse insertion into a bodily substrate, for example, resected bone. A surgical template—for example, to assist in sawing, drilling with a drill bit and drill guide, and broaching with a broach—along with such bone removal tools can help prepare the bone for receipt of the rail-fixing implant.

And so, the present invention is provided. Various feature(s), part(s), step(s), subcombination(s) and/or combination(s) can be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

What is claimed is:

1. An ankle arthroplasty implant device comprising:
    first and second implant bodies for implanting in respective talar and tibial bones of a patient, the first body including a truncated, convex spherically shaped dome articular surface, and the second body including a truncated, concave spherically shaped socket articular surface for operatively engaging with said dome; and
    first and second transversely elongated wedge-shaped stems on the first implant body and third and fourth transversely elongated wedge-shaped stems on the second implant body, each of said first, second, third and fourth wedge-shaped stems having leading and pursuing ends, each of which has one and only one wall projecting from its respective body and in its entirety substantially orthogonal thereto at an outer boundary of said body, and including respective spaced apart side walls angling laterally outwardly away from one another from the respective leading toward the pursuing ends to form respective dovetail configurations.

2. The ankle arthroplasty implant device of claim 1, which is made of a material selected from the group consisting of a metal and a ceramic.

3. The ankle arthroplasty implant device of claim 2, wherein the outer boundary of said body is substantially circular when viewed from a top or bottom position.

4. The ankle arthroplasty implant device of claim 3, wherein each of said first, second, third and fourth stems is configured to angle the respective spaced apart side walls laterally outwardly away from one another at an angle about from 3 to 5 degrees.

5. A combination comprising, in kit form, (A) an improved implant or implant component device and (B) a resection template tool for preparation of a bodily substrate for implantation of the improved implant or implant component device, wherein:
    (A) the improved implant or implant component device comprises, in an implant or implant component device comprising a load-bearing implant or component therefor, which bears load substantially in a load-bearing direction when implanted, and which includes the following:
        at least one implant body, each having connected thereto one and only one transverse stem, which runs in a first transverse direction substantially perpendicular to the load-bearing direction, and which has along the first transverse direction a leading element and a pursuing element, with:
            the leading element having and terminating in a leading element wall projecting from the at least one implant body, which has a lateral or radial dimension along a second transverse direction essentially perpendicular to the first transverse direction and substantially perpendicular to the load-bearing direction that is less than that of the pursuing element;
            the pursuing element having and originating in a pursuing element wall projecting from the at least one implant body, which has a lateral or radial dimension along said second transverse direction but spaced apart from the leading element wall; and
        each of the leading and pursuing element walls projecting in its entirety substantially perpendicular from the pertinent at least one implant body;
        which one and only one transverse stem has between the leading and pursuing elements two spaced apart outside side walls projecting from the at least one implant body, wherein each of the leading and pursuing element walls separately connect with the two spaced apart outside side side walls, wherein:
            the leading element wall is not greater than a lateral or radial distance between the two spaced apart outside side walls about the leading element; and the pursuing element wall is not substantially greater than a lateral or radial distance between the two spaced apart outside side walls about the pursuing element;

with the one and only one transverse stem adapted for transverse insertion into resected bone configured for complementary female reception of the one and only one transverse stem such that the one and only one transverse stem has a laterally disposed feature for providing stopping of the one and only one transverse stem along a path it takes in its traverse insertion into said bone; and on the at least one implant body, away from and generally opposing the one and only one transverse stem, a surface for articulation— the improvement which comprises:

a void volume spanning from the leading element to the pursuing element and running in the first transverse direction substantially perpendicular to the load-bearing direction substantially having laterally in the second transverse direction essentially perpendicular to the first transverse direction and substantially perpendicular to the load-bearing direction a plurality of opposing inner walls, so as to form from the one and only one transverse stem a transverse rail stem system including a plurality of separate transverse rails, each transverse rail having a rail leading element and a rail pursuing element;

the transverse rail stem system being adapted for insertion into resected bone configured for complementary female reception of the transverse rail stem system such that the transverse rail stem system has at least one laterally disposed feature for providing lateral stopping of the transverse rail stem system after insertion into said bone;

provided that the at least one implant body is not one which is adapted for arthroplasty of opposing spinal vertebrae such that the improved implant or implant component device is not a spinal vertebral implant; and (B) the resection template tool comprises a tool body having a substantially thick disc form having a first surface, a second surface for engaging resected bone opposing but not confronting the first surface, and an outer wall boundary connecting the first and second surfaces, and a plurality of opposing grooves in the first surface, each of which open through the outer wall boundary at two locations, into each of which a bone broach can be inserted and guided so as to configure lateral walls in the bone for the complementary female reception of the transverse rail stem system.

6. The combination of claim 5, wherein the at least one laterally disposed feature for providing stopping of the transverse stem is a wedge with respect to the two spaced apart outside side walls projecting from the at least one implant body.

7. The combination of claim 6, wherein each of the separate transverse rails is in a form of a wedge such that the improved implant or implant component device is adapted for transverse insertion into said bone and provides for lateral stopping of the transverse rail stem system along a path it takes in the transverse insertion into said bone.

8. The combination of claim 7, wherein each wedge is in a form of a dove-tail wedge such that both lateral and plumb holding forces are provided.

9. The combination of claim 8, wherein the at least one implant body is part of an ensemble for total joint arthroplasty of an articulating joint, which has, as the at least one implant body, two implant bodies, each having the transverse rail stem system, with each transverse rail system having two and only two transverse rails, wherein:

each transverse rail stem system is adapted for implantation into separate resected bones and configured for complementary female reception of the transverse rail stem system in said bones, which are resected bones of the joint; and each improved implant or implant component device includes the surface for articulation such that the surface for articulation on one of the two implant bodies is complementary to and can articulate against the surface for articulation on the other of the two implant bodies when the ensemble is implanted.

10. The combination of claim 9, wherein the improved implant or implant component device is adapted for an articulating joint of an ankle, which provides for excellent post-surgery recovery and mobility.

11. The combination of claim 7, wherein the at least one implant body is adapted for arthroplasty of an articulating joint, with the transverse rail stem system adapted for implantation into said bone, which is resected bone of the joint, selected from the group consisting of a glenoid bone, a patella, a radial head of a long bone other than an ankle, and a digit such that the improved implant or implant component device is selected from the group consisting of a glenoid implant, a patellar implant, an implant for a radial head of a long bone other than an ankle, and a digital implant.

12. A combination comprising, in kit form: (A) a joint prosthesis apparatus for implant at a selected transverse location in an articulating, weight bearing joint space presenting male and female joint components, the joint components having a predetermined transverse width and being formed with respective through, elongated wedge shaped, dovetail, transverse resection channels located at selected positions in the respective joint components and being of a predetermined shape, having opposite dovetail sides converging linearly along their lengths at a selected angle with respect to one another in the transverse direction from respective wide channel openings formed to open to the respective one transverse side of the joint and narrower channel openings formed to open on the transverse side of the joint opposite the one transverse side, the joint prosthesis apparatus including:

prosthesis devices to implant in the articulating joint space, each of these having a body with a substrate-interfacing element, with a first of the devices including a truncated concave sphere shaped socket and a second of the devices including a truncated convex sphere shaped ball element to be received complementarily in the socket, wherein the substrate-interfacing element in the first of these devices is opposite but not confronting the socket and the substrate-interfacing element in the second of these devices is opposite but not confronting the ball element;

each of the prosthesis devices including a pair of axial stems, each stem configured with opposite dovetail shaped stem side walls diverging linearly away from one another at the selected angle in a transverse wedge shape with a narrow leading end and a wide trailing end and constructed to be received transversely from the respective wide channel openings to be nested in close fit relationship in the respective resection channel to wedge against the side walls of the resected channels located at the selected location such that a surgeon can extend a bone-resecting instrument fully through in the lateral direction across the joint components to form the resection channels with channel side walls angling toward one another at the selected angle to define the predetermined shape in the joint components;

the devices selected and the stems introduced through the wide openings of the respective channels to be driven transversely into the channels from the wide channel openings to wedge the stems in close fit relationship in the respective channels at the selected location; and (B) at least one template tool to be disposed adjacent the joint components, wherein the at least one template tool includes a tool body in substantially thick disc form having a first surface, a second surface opposing but not confronting the first surface, and an outer wall boundary connecting the first and second surfaces, the tool body constructed with a pair of guide grooves diverging away from one another at the selected angles, each guide groove passing through the first surface and, at two locations, the outer wall boundary, and configured and oriented to receive the bone-resecting instrument to project therefrom to form transverse resection channels for at least one of the joint components for receipt of one of the prosthesis devices configured with the predetermined shape.

13. The combination of claim 12, wherein the joint prosthesis apparatus is useful for implant in a dysfunctional ankle and for providing excellent post-surgery recovery and mobility, replacing tibial and talar joint components, wherein the stems are constructed with respective lateral lengths sufficient, when implanted, to project substantially laterally across transverse widths of the tibial and talar joint components.

* * * * *